United States Patent [19]

Shiragami et al.

[11] Patent Number: 5,336,770
[45] Date of Patent: Aug. 9, 1994

[54] TRANSGLYCOSILATION PROCESS FOR PRODUCING ACYCLIC NUCLEOSIDES

[75] Inventors: Hiroshi Shiragami; Yoshihito Koguchi; Kunisuke Izawa, all of Kawasaki, Japan

[73] Assignee: Ajinomoto Co., Inc., Tokyo, Japan

[21] Appl. No.: 917,357

[22] Filed: Jul. 23, 1992

[30] Foreign Application Priority Data

Sep. 18, 1991 [JP] Japan .................. 3-238247

[51] Int. Cl.$^5$ .................. C07D 473/18; C07B 43/04
[52] U.S. Cl. .................. 544/276; 544/277
[58] Field of Search .................. 544/276, 277

[56] References Cited

U.S. PATENT DOCUMENTS 4,199,574  4/1980  Schaeffer .
4,835,104  5/1989  Yokozeki et al. .

FOREIGN PATENT DOCUMENTS 0090417  10/1983  European Pat. Off. .
0275065   7/1988  European Pat. Off. .

OTHER PUBLICATIONS

Nucleosides and Nucleotides, vol. 6, Nos. 1 and 2, 1987, pp. 385–386, J. Boryski, et al., "Transglycosylation of Guanine Nucleosides".

Nucleosides & Nucleotides, vol. 8, No. 4, 1989, pp. 529–536, J. Boryski, et al., "Application of the Transpurination Reaction to Synthesis of Acyclic Guanosine Analogues".

Database WPIL, Derwent Publications Ltd., AN 86-012206, SU-A-961 354, Aug. 7, 1985.

*Primary Examiner*—Mark L. Berch
*Attorney, Agent, or Firm*—Oblon, Spivak, McClelland, Maier & Neustadt

[57] ABSTRACT

Herein is disclosed a novel and industrially advantageous process for synthesizing acyclic nucleosides such as acyclovir and ganciclovir from ribonucleosides, which process comprises adding an acid catalyst and an acid anhydride to a solution of a ribonucleoside such as guanosine and an ester derivative of an acyclic sugar, and heating the mixture, whereby a transglycosilation reaction takes place between the ribose moiety of the ribonucleoside and the ester derivative of the acyclic sugar.

2 Claims, No Drawings

TRANSGLYCOSILATION PROCESS FOR PRODUCING ACYCLIC NUCLEOSIDES

BACKGROUND OF THE INVENTION

1. Field of the Invention

The present invention concerns a process for producing acyclic nucleosides, such as, particularly, acyclovir of the below-mentioned formula (IV) and ganciclovir of the below-mentioned formula (V), both being an antiviral agent. Acyclovir and ganciclovir are compounds having a powerful anti-viral activity, particularly, to herpes virus both in vitro and in vivo, and have already been authorized and sold commercially as an anti-viral chemotherapeutical agent.

2. Discussion of the Background

For the purpose of producing acyclovir or ganciclovir, there has been known, for example, a method of using guanine as a starting material or a method of using 2,6-dichloropurine or 2-amino-6-chloropurine. However, each of the methods has drawbacks in that the desired compound can not be obtained in a high yield, the desired compound can not be obtained easily in a high purity, and the procedures concerned are complicated from the industrial point of view. U.S. Pat. No. 4,199,574; J. R. Barrio et al., J. Med. Chem., 23 572 (1980); and J. C. Martin et al., J. Med. Chem., 26, 759, (1983).

On the other hand, ribonucleosides such as guanosine, adenosine and inosine have been mass-produced by a fermentation process. In view of the above, it has been an important subject to develop a novel and industrially advantageous process for synthesizing acyclic nucleosides such as acyclovir and ganciclovir from the above-mentioned ribonucleosides.

SUMMARY OF THE INVENTION

Accordingly, an object of the present invention is to provide a novel and industrially advantageous process for synthesizing acyclic nucleosides such as acyclovir and ganciclovir from ribonucleosides mass-produced by fermentation. Other objects will become apparent from the description of the present invention given hereinbelow.

In an aspect of the present invention, there is provided a process for producing an acyclic nucleoside derivative of the formula (I):

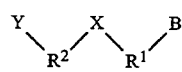
(I)

which comprises reacting a ribonucloside derivative of the formula (II):

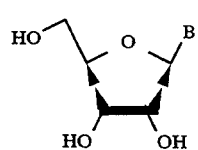
(II)

with an acid anhydride and an ester derivative of the formula (III):

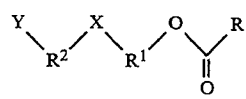
(III)

in the presence of an acid catalyst.

In another aspects of the present invention, there is provided a process for producing a nucleoside derivative of the general formula (VII):

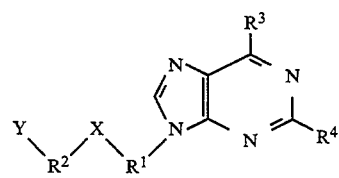
(VII)

which comprises heating a purine derivative of the general formula (VI):

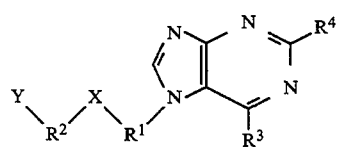
(VI)

in the presence of an acid catalyst.

Other aspects will become apparent from the description of the present invention given hereinbelow.

DETAILED DESCRIPTION OF THE INVENTION

With the subject in mind, the present inventors have made profound studies on the transglycosilation reactions between guanosine and a derivative of the sugar moiety of acyclic nucleosides. As a result, it has been found that a transglycosilation reaction takes place between the ribose moiety of a ribonucleoside and an ester derivative of a acyclic sugar when an appropriate acid catalyst and a carboxylic acid anhydride are added to a mixture of a ribonucleoside such as guanosine and an ester derivative of an acyclic sugar and the resultant mixture is heated. The present invention has been made on these findings.

That is, the present invention concerns a process for producing an acyclic nucleoside derivative represented by the general formula (I):

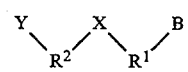
(I)

where B represents a purine base or pyrimidine base which may be substituted, $R^1$ and $R^2$ which may be identical with, or different from, each other represent an alkylene group with 1 to 4 carbon atoms which may be substituted with hydroxyl group (s), amino group (s), alkoxyl group (s), silyl group (s), alkoxycarbonyl group (s), acyl group (s) and/or halogen atom(s), X represents an oxygen atom, a sulfur atom, an imino group or a methylene group, and Y represents a hydroxyl group, an amino group, an alkoxyl group, a silyl ether group, an alkoxycarbonyl group, an acyl group or a halogen atom, which comprises reacting a ribonucleoside derivative represented by the general formula (II):

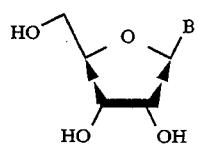

(II)

where B represents a purine base or pyrimidine base which may be substituted, in the presence of an acid catalyst, with an acid anhydride and an ester derivative represented by the general formula (III):

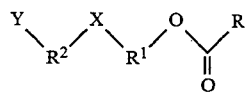

(III)

where R represents a hydrogen atom, an alkyl group with 1 to 20 carbon atoms or an aryl group with 6 to 20 carbon atoms, $R^1$ and $R^2$ which may be identical with, or different from, each other represent an alkylene group with 1 to 4 carbon atoms which may be substituted with hydroxyl group(s), amino group(s), alkoxyl group(s), silyl group(s), alkoxycarbonyl group(s), acyl group(s) and/or halogen atom(s), X represents an oxygen atom, a sulfur atom, an imino group or a metylene group, and Y represents a hydroxyl group, an amino group, an alkoxyl group, a silyl ether group, an alkoxycarbonyl group, an acyl group or a halogen atom.

The present invention also concerns a process for producing a nucleoside derivative represented by the general formula (VII):

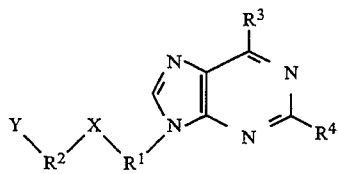

(VII)

where $R^1$ and $R^2$ which may be identical with, or different from, each other represent an alkylene group with 1 to 4 carbon atoms which may be substituted with hydroxyl group(s), amino group(s), alkoxyl group(s), silyl group(s), alkoxycarbonyl group(s), acyl group(s) and/or halogen atom(s), X represents an oxygen atom, a sulfur atom, an imino group or a methylene group, Y represents a hydroxyl group, an amino group, an alkoxyl group, a silyl ether group, an alkoxycarbonyl group, an acyl group or a halogen atom, and $R^3$ and $R^4$ each represent independently a hydrogen atom, a halogen atom, hydroxyl group, an amino group or a mercapto group, said hydroxyl group, amino group and mercapto group each being, if desired, substituted with an alkyl group, an aryl group, a silyl group or an acyl group, which comprises heating, in the presence of an acid catalyst, a purine derivative represented by the general formula (VI):

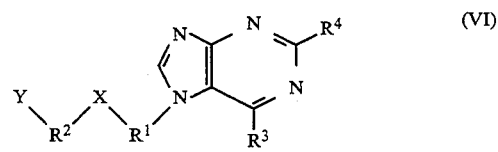

(VI)

where $R^1$ and $R^2$ which may be identical with, or different from, each other represent an alkylene group with 1 to 4 carbon atoms which may be substituted with hydroxyl group(s), amino group(s), alkoxyl group(s), silyl group(s), alkoxycarbonyl group(s), acyl group(s) or halogen atom(s), X represents an oxygen atom, a sulfur atom, an imino group or a methylene group, Y represent a hydroxyl group, an amino group, an alkoxyl group, a silyl ether group, an alkoxycarbonyl group, an acyl group or a halogen atom, and $R^3$ and $R^4$ each represent independently a hydrogen atom, a halogen atom, a hydroxyl group, an amino group or mercapto group, said hydroxyl group, an amino group and a mercapto group each being, if desired, substituted with an alkyl group, an aryl group, a silyl group or an acyl group.

The present invention will now be described specifically illustrating a synthetic process for acyclovir of the formula (IV) and ganciclovir of the formula (V) with reference to Schemes I(a) and I(b).

Scheme I(a)

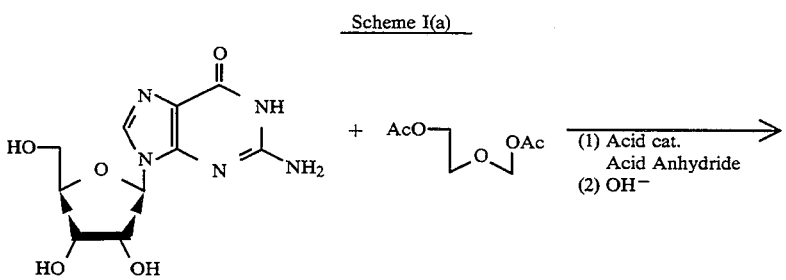

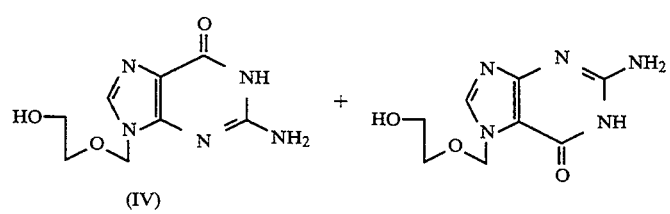

(IV)

Scheme I(b)

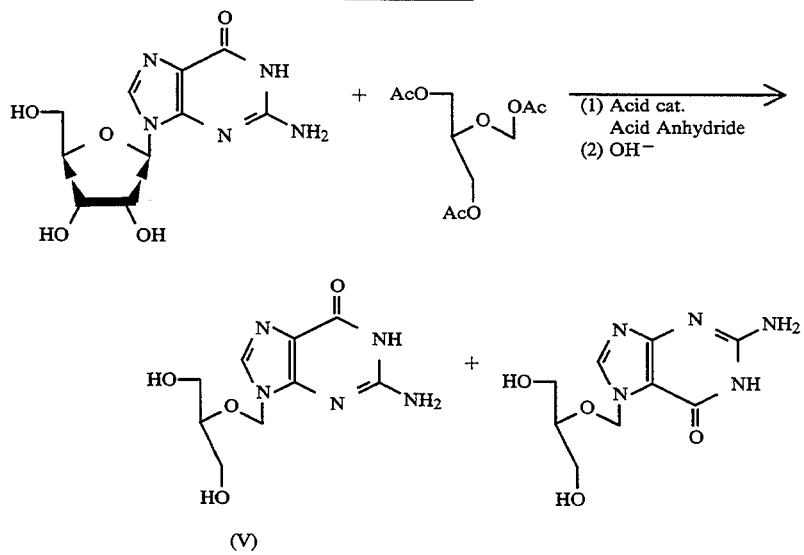

(V)

When, e.g., acetic anhydride and, e.g., p-toluenesulfonic acid monohydrate are added to a mixed solution of guanosine and 2-oxa-1,4-butanediol diacetate, and the resultant mixture is heated at, e.g., 100° C. for, e.g., 24 hours, a transglycosilation reaction takes place between the moiety of guanosine ribose and 2-oxa-1,4-butanediol diacetate. After completion of the reaction, the reaction solution is subjected to, e.g., alkaline hydrolysis, whereby acyclovir of the formula (IV) is obtained. In this transglycosilation reaction, the 7-position isomer of the acyclovir is also formed together with acyclovir. The two isomers can be separated, if necessary, from each other by, e.g., silica gel column chromatography or recrystallization.

On the other hand, when, e.g., acetic anhydride and, e.g., p-toluenesulfonic acid monohydrate are added to a mixed solution of guanosine and acetoxymethyl-2,3-diacetoxy-1-propyl ether, the resultant mixture is heated at, e.g., 100° C. for, e.g., 24 hours, and then the reaction solution is subjected to, e.g., alkaline hydrolysis, ganciclovir of the formula (V) is obtained. Also, in this transglycosilation reaction, the 7-position isomer of ganciclovir is by-produced. The two isomers can be separated, if necessary, from each other by e.g., silica gel column chromatography or recrystallization.

According to the present invention, in what amount an ester derivative of the formula (III) should be used on the basis of a ribonucleoside of the formula (II) is not critical, and usually a ratio of 1–2:1 is chosen.

As for the acid anhydride of the present invention, an organic carboxylic acid anhydride such as acetic anhydride, propionic anhydride or benzoic anhydride or a phosphoric acid anhydride such as pyrophosphoric acid or metaphosphoric acid is used. The amount to be used is from about 1 to about 10 equivalents based on the starting material of the formula (II).

As for the acid catalyst of the present invention, acid catalysts such as organic acids, inorganic acids and Lewis acids, e.g., p-toluenesulfonic acid monohydrate, sulfanilic acid, methanesulfonic acid, trifluoroacetic acid, trifluoroboron ether complexes, sulfuric acid, phosphoric acid, and hydrochloric acid, are in general used. The catalyst is used in an amount from 1 to 20 mol % based on the starting material of the formula (II).

As for the reaction solvent, usual organic solvents such as, e.g., dimethylformamide; dimethylsulfoxide; acetonitrile; carboxylic acid esters such as ethyl acetate and methyl acetate; hydrocarbons such as benzene, hexane and toluene; ethers such as diethyl ether, tetrahydrofuran and dioxane; halogenated hydrocarbons such as dichloromethane, chloroform and dichloroethane; ketones such as acetone and methyl ethyl ketone; are used. If a compound of the formula (II) is soluble in a compound of the formula (III) and an acid anhydride, the reaction of the present invention may be conducted without any solvent.

The reaction temperature is usually selected from within a temperature range of 20° to 200° C., while the reaction time is usually selected from a period of 1 hour to 1 week.

As for the ribonucleoside derivatives of the formula (II), purine nucleosides such as guanosine, adenosine and inosine, pyrimidine nucleosides such as uridine and cytidine, and the derivatives of the base moiety of such nucleoside may be used.

The acyclic sugar ester derivatives of the present invention have the structure as shown by the formula (III), having an acyl group at the terminal end. There can be mentioned, e.g., 2-oxa-1,4-butanediol diacetate as the acyclic sugar ester derivative, which can be, in turn, synthesized by reacting 1,3-dioxolane and acetic anhydride in the presence of a catalytic amount of an acid. Acyclic sugar ester derivatives thus obtained are allowed to react with ribonucleoside derivatives with or without isolation.

A desired reaction product such as acyclovir or ganciclovir can be isolated from the reaction mixture, e.g., by the treatment with an alkaline solution, followed by purification with silica gel column chromatography.

Next, the isomerization reaction will be explained.

In the transglycosilation reaction, as has already been described regarding the production of acyclovir and ganciclovir, when a purine nucleoside such as guanosine, adenosine or inosine is used as the ribonucleoside, the 7-position isomer is formed together with the 9-position isomer.

When the desired compound is a 9-position isomer such as acyclovir, isomerization of the 7-position isomer to the desired compound (a 9-position isomer) is required. The present inventors have made a study thereon, and as a result, found that the expected isomerization reaction may be realized, with the solvent distilled off or replaced with another solvent, or without isolation of the intermediate from the reaction mixture after the transglycosilation reaction by continuing the heating of the intermediate in the presence of an acid catalyst.

As shown in Scheme II, the 7-position isomer can be isomerized by heating in the presence of an acid catalyst, in the absence, or in the presence, of an appropriate solvent into the 9-position isomer such as an acyclovir derivative or a ganciclovir derivative.

Scheme II

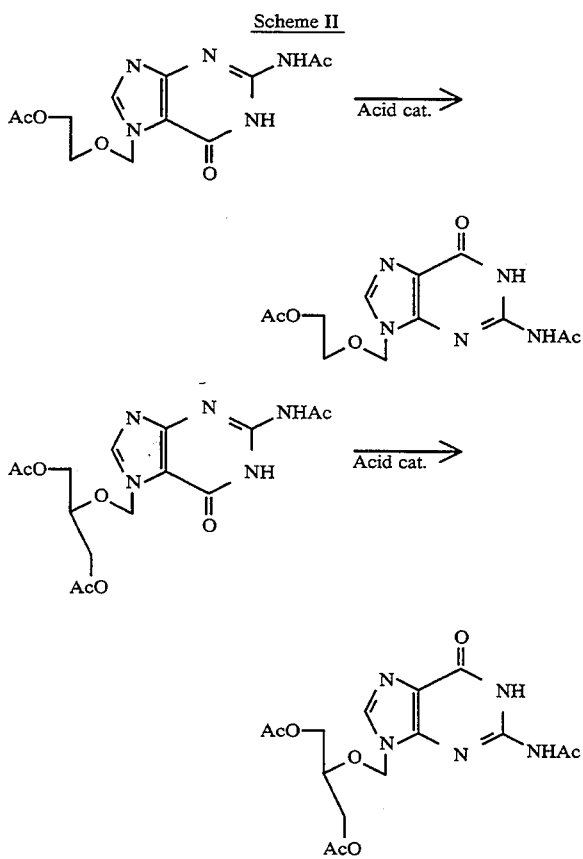

As for the solvent for the isomerization reaction, there can be mentioned usual organic solvents such as, e.g., carboxylic acid esters such as ethyl acetate and methyl acetate; hydrocarbons such as benzene, hexane and toluene; ethers such as diethyl ether, tetrahydrofuran and dioxane; halogenated hydrocarbons such as dichloromethane, chloroform and dichloroethane; and ketones such as acetone and methyl ethyl ketone.

The reaction is usually conducted at a temperature of 20° to 200° C., while the reaction time is usually 1 hour to 1 week.

The completion of the isomerization reaction can be confirmed by, e.g., high performance liquid chromatography. The resultant acyclovir and ganciclovir derivatives form crystals and can be isolated easily.

These derivatives give the final products, i.e., acyclovir and ganciclovir by, e.g., alkaline hydrolysis.

EXAMPLES:

Example 1: Synthesis of 9- ((2-acetoxyethoxy) methyl) -$N^2$-acetyl guanine and 7-((2-acetoxyethoxy)-methyl)-$N^2$-acetyl guanine from guanosine (1 of 2).

To 10 g of guanosine, 13 g of 2-oxa-1,4-butanediol diacetate (2 eq.), 36 g of acetic anhydride (10 eq.), 100 ml of dimethylformamide and 0.67 g (2.5 mol %) of p-toluenesulfonic acid monohydrate were added, and the mixture was stirred at 100° C. for 18 hours.

It was confirmed by comparison with authentic samples using high performance liquid chromatography that 9-((2-acetoxyethoxy)methyl)-$N^2$-acetylguanine and 7-((2-acetoxyethoxy) metyl) $N^2$-acetylguanine had been formed in 48% and 19% yields based on the guanosine, respectively, namely, at a ratio of 2.5:1.

Example 2: Synthesis of 9- ((2-acetoxyethoxy) methyl) -$N^2$-acetylguanine and 7-((2-acetoxyethoxy) methyl)-$N^2$-acetylguanine from guanosine (2 of 2).

To 10 g of guanosine, 5.2 g of 1,3-dioxolane (2 eq.), 36 g of acetic anhydride (10 eq.), 100 ml of dimethylformamide and 0.67 g (2.5 mol %) of p-toluenesulfonic acid monohydrate were added, and the mixture was stirred at 100° C. for 18 hours.

2-oxa-1,4-butanediol diacetate was in situ formed in the reaction system and, via the same reaction as in Example 1, it was confirmed that 9-((2acetoxyethoxy) methyl)-$N^2$-acetylguanine and 7-((2acetoxyethoxy) methyl) -$N^2$-acetylguanine had been formed in 46% and 18% yields based on the guanosine, respectively, by comparison with authentic samples using high performance liquid chromatography.

Example 3: Isomerization of 7-((2-acetoxyethoxy)methyl)-$N^2$-acetylguanine into 9-((acetoxyethoxy) methyl)-$N^2$-acetylguanine.

The reaction mixture obtained in Example 1 was directly subjected to distillation under a reduced pressure of 5 mmHg to remove the solvent, and the syrup residue was stirred at 100° C. for 18 hours, whereby 9-((2-acetoxyethoxy)methyl)-$N^2$-acetylguanine and 7-((2-acetoxyethoxy) methyl)-$N^2$-acetyl-guanine were obtained at a resulting ratio of 8.4:1.

The resulting reaction mixture was subjected to purification using column chromatography with 100 g of silica gel, whereby 6.7 g of 9-((2-acetoxyethoxy)methyl)-$N^2$-acetylguanine was obtained. Yield, 61%.

$^1$H NMR (300 MHz, DMSO-$d_6$) analytical values: δ, 1.95 (3H, s, Ac), 2.17 (3H, s, Ac), 3.63–3.73 (2H, m, H-3'), 4.05–4.11 (2H, m, H-4'), 5.48 (2H, s, H-1'), 8.13 (1H, s, H-8) .

Mass spectral analytical value: MH$^+$ =310.

Example 4: Synthesis of acyclovir from 9-((2-acetoxyethoxy) methyl)-$N^2$-acetylguanine.

To 5.0 g of 9-((2-acetoxyethoxy)methyl)-$N^2$ -acetylguanine was added 50 ml of an aqueous 5% sodium hydroxide solution, and the mixture was sitrred for 24 hours at room temperature for reaction.

The resulting reaction solution was neutralized with 1N hydrochloric acid, and the precipitated crystals were collected by filtration, whereby 3.2 g of acyclovir was obtained. Yield, 92% .

$^1$H NMR (300 MHz, DMSO-$d_6$) analytical values: δ, 3.47 (4H, brs, H-3' & 4'), 4.66 (1H, brs, OH), 5.35 (2H, s, H-1'), 6.49 (2H, brs, NH$_2$), 7.81 (1H, s. H-8).

Mass spectral analytical value: MH$^+$ =226.

Example 5: Synthesis of 9-((1,3-diacetoxy-2-propoxy)methyl)-$N^2$-acetylguanine from guanosine.

To 10 g of guanosine, 17.5 g of 1,4-diacetoxy-3-acetoxymethyl-2-oxa-butane (2 equivalent), 36 g of acetic anhydride (10 equivalent), 100 ml of dimethylformamide and 0.67 g (2.5 mol %) of p-toluenesulfonic acid monohydrate were added, and the mixture was stirred at 100° C. for 18 hours for reaction. Subsequently, the solvent was distilled off under a reduced pressure of 5 mmHg, and the syrup residue was stirred at 100° C. for 18 hours.

Subsequently, the syrup was subjected to column chromatography using 300 g of silica gel and purified by eluting with a 7:1 mixed solvent of chloroform and methanol, whereby 6.9 g of 9-((1,3-diacetoxy-2-propoxy) methyl)-N²-acetylguanine was obtained. Yield, 51%.

¹H NMR (300 MHz, CDCl₃) analytical values: δ, 7.78 (1H, s, H-7), 5.51 (2H, s, H-1'), 4.50–4.06 (4H, m, H-4', H-5'), 2.62 (3H, s, NHAc), 2.03 (4H, s, OAcx2).

Mass spectral analytical value: MH+ =382.

Example 6: Synthesis of ganciclovir from 9-((1,3-diacetoxy-2-propoxy)methyl)-N²-acetylguanine.

To 5.0 g of 9-((1,3-diacetoxy-2-propoxy)methyl)-N²-acetylguanine was added 50 ml of an aqueous 5% sodium hydroxide solution, and the mixture was stirred for 24 hours at room temperature for reaction.

The resulting reaction solution was neutralized with 1N hydrochloric acid, and the precipitated crystals were collected by filtration, whereby 3.0 g of gunciclovir was obtained. Yield, 90% .

¹H NMR (300 MHz, DMSO-d₆) analytical values: δ, 8.31 (2H, s, NH₂), 7.58 (1H, s, H-8), 5.43 (2H, s, H-1'), 3.62–3.28 (5H, m, H-3', H-4', H-5) .

Mass spectrum analytical value: MNa+ =278.

Example 7: Synthesis of 9-((2-acetoxyethoxy)methyl)-adenine (in the formula (I), R¹=CH₂, R²=(CH₂)₂, X=O, and Y=OH) from adenosine.

To 10 g of adenosine, 12 g of 2-oxa-1,4-butanediol diacetate (2 eq.), 34 g of acetic anhydride (10 eq.), 100 ml of acetonitrile and 0.63 g (2.5 mol %) of p-toluenesulfonic acid monohydrate were added, and the mixture was refluxed with stirring at an elevated temperature for 48 hours for reaction. Then, the solvent was removed by distillation under reduced pressure from the reaction mixture, and the residue was subjected to hydrolysis with aq. NaOH.

After neutralization, purification using the synthetic adsorption resin "SP-207" was carried out, whereby 5.4 g of the desired product was obtained. Yield, 69%.

¹H NMR (300 MHz, DMSO-d₆) analytical values: δ, 3.46 (4H, s, H-2' & 3'), 4.50 (1H, brs, OH), 5.25 (2H, s, H-1'), 7.00 (2H, s, NH₂), 8.17 (1H, s, H-2), 8.20 (2H, s, H-8) .

Mass spectral analytical value: MH+ =210.

Example 8: Synthesis of 9-((2-acetoxyethoxy)methyl)-hypoxanthine (in the formula (I), R¹=CH₂, R²=(CH₂)₂, X=O, and Y=OH) from inosine.

To 10 g of inosine, 12 g of 2-oxa-1,4-butanediol diacetate (2 eq. ), 34 g of acetic anhydride (10 eq. ), 100 ml of acetonitrile and 0.63 g (2.5 mol %) of p-toluenesulfonic acid monohydrate were added, and the mixture was refluxed with stirring at an elevated temperature for 48 hours for reaction. Then, the solvent was removed by distillation under reduced pressure from the reaction mixture, and the residue was subjected to hydrolysis with aq. NaOH.

After neutralization, purification using the synthetic adsorption resin "SP-207" was carried out, whereby 3.7 g of the desired product was obtained. Yield, 47%.

¹H NMR (300 MHz, DMSO-d₆) analytical values: δ, 3.44 (4H, s, H-2' & 3'), 4.30 (1H, brs, OH), 5.27 (2H, s, H-1'), 8.05 (1H, s, H-2), 8.31 (2H, s, H-8).

Mass spectrum analytical value: MH+ =211.

Example 9: Synthesis of 9-((2-acetoxyethoxy) methyl) -N²-acetylguanine and 7-((2-acetoxyethoxy) methyl)-N²-acetylguanine from guanosine.

To a mixture of 252.26 g of acetic anhydride and 52.36 g of 1,3-dioxolane was added 6.70 g of p-toluenesulfonic acid monohydrate. The mixture was stirred for 1 hour, added with 100 g of guanosine, and stirred at 100° C. for further 24 hours.

It was confirmed that 9-((2-acetoxyethoxy) methyl) -N²-acetylguanine and 7-((2-acetoxyethoxy) methyl) -N²-acetylguanine had been formed in 46% and 31% yields, respectively, by comparison with authentic samples using high performance liquid chromatography.

What is claimed is:

1. A process for producing 9-((2-hydroxyethoxy)-methyl)guanine represented by the formula (IV):

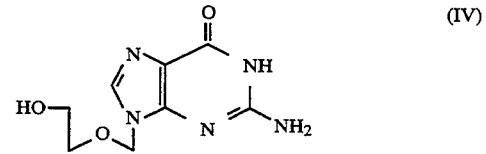

(IV)

which comprises reacting guanosine, under an acid catalyst, with an acid anhydride and 2-oxa-1,4-butanediol diacetate, followed by saponification.

2. A process for producing 9-((1,3-dihydroxy-2-propoxy) methyl)guanine represented by the formula (V):

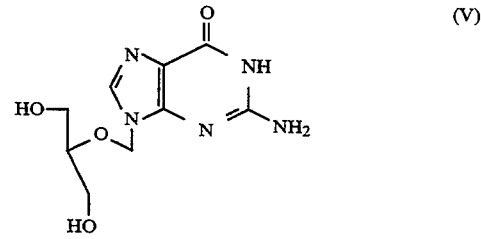

(V)

which comprises reacting guanosine, under an acid catalyst, with an acid anhydride and acetoxymethyl-2,3-diacetoxy-1-propyl ether, followed by saponification.

* * * * *